United States Patent [19]
Lattrell et al.

[11] Patent Number: 5,629,288
[45] Date of Patent: May 13, 1997

[54] LIPOPEPTIDE DERIVATIVES, A PROCESS FOR THEIR PREPARATION AND THEIR USE

[75] Inventors: Rudolf Lattrell, Königstein; Theodor Wollmann, Hofheim; Holger Wallmeier, Sulzbach; Peter Hammann, Babenhausen; Dieter Isert, Eschborn, all of Germany

[73] Assignee: Hoechst Aktiengesellschaft, Frankfurt am Main, Germany

[21] Appl. No.: 411,931

[22] Filed: Mar. 28, 1995

[30]  Foreign Application Priority Data

Mar. 30, 1994 [DE] Germany .................... 44 11 025.1

[51] Int. Cl.$^6$ .................................... A61K 38/08
[52] U.S. Cl. .................. 514/9; 514/11; 530/317
[58] Field of Search ............... 514/9, 11; 530/317

[56]  References Cited

FOREIGN PATENT DOCUMENTS 0629636  12/1994  European Pat. Off. .

OTHER PUBLICATIONS

Debono et al., "Enzymatic and Chemical Modifications of Lipopeptide Antibiotic A21978C: The Synthesis and Evaluation of Daptomycin (LY146032)", Journal of Antibiotics, 41(8):1093–1105 (1988).

Allen et al., "Biosynthesis of Modified Peptidoglycan Precursors by Vancomycin–resistant *Enterococcus Faecium*", FEMS Microbiology Letters, 98:109–116 (1992).

Altmann et al., "Die Chemische Synthese von Peptiden und Proteinen", Chemie in Unsere Zeit, 27(6):274–286 (1993).

Shoji et al., "Studies on Tsushimycin, II The Structures of Constituent Fatty Acids," *The Journal of Antibiotics*, vol. XXII, No. 10, 1969, pp. 473–479.

Strong et al., "Studies on the Amino Acid Sequence of Amphomycin," *Antimicrobial Agents and Chemotherapy*, 1970, pp. 42–45.

*Primary Examiner*—Edward J. Cain
*Attorney, Agent, or Firm*—Finnegan, Henderson, Farabow, Garrett & Dunner, L.L.P.

[57]  ABSTRACT

Lipopeptide derivatives of the formula I

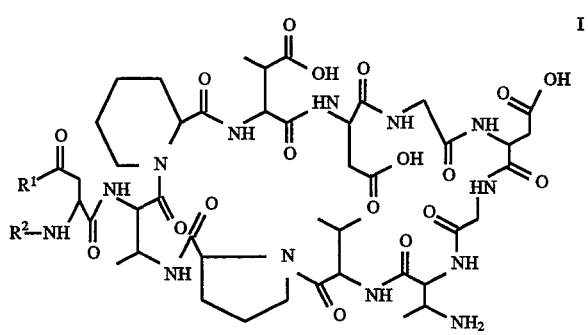

with $R^1$ equal to OH or $NH_2$ and $R^2$ a $C_8$–$C_{22}$-acyl radical, pharmaceutical products which are effective for bacterial infections and contain such lipopeptide derivatives, process for preparing the lipopeptide derivatives and the pharmaceutical products, and the use of the lipopeptide derivatives for controlling bacterial infections are described.

19 Claims, No Drawings

LIPOPEPTIDE DERIVATIVES, A PROCESS FOR THEIR PREPARATION AND THEIR USE

The invention relates to derivatives of antibiotics of the lipopeptide complex A 1437, to a process for their preparation and to their use as pharmaceuticals.

European Patent Application No. 0 629 636 proposes lipopeptides which have very homologous amino acid sequences but different fatty acid residues (lipid portion) and which are synthesized by *Actinoplanes sp.* during the fermentation and released into the culture medium, as well as a process for isolating the lipopeptides from the culture medium, their purification and the use of the lipopeptides as pharmacological active substances, in particular against Gram-positive bacteria.

The object of this invention is now to look for derivatives of the lipopeptide complex A 1437 with a lower toxicity than the natural A 1437 lipopeptides.

This object is achieved according to the invention by derivatives according to a compound of the formula I.

The invention therefore relates to:

1. Lipopeptide A 1437 derivatives of the formula I in which
$R^1$ is OH or $NH_2$,
$R^2$ is a straight-chain or branched, saturated or unsaturated aliphatic $C_8$–$C_{22}$-acyl radical which may be interrupted by phenyl or cycloalkyl groups or by oxygen,
and the pharmaceutically acceptable salts thereof.

2. A process for preparing a compound of the formula I, which comprises reacting a compound of the formula II in which
$R^1$ has the abovementioned meaning, and
$R^3$ is an amino protective group known from peptide chemistry, preferably the tert-butoxycarbonyl (BOC), the benzyloxycarbonyl (Z, Cbz), the fluorenylmethoxycarbonyl (Fmoc) or the allyloxycarbonyl (Alloc) protective group, with a carboxylic acid of the formula III $$R^2OH \qquad III$$

in which
$R^2$ has the abovementioned meanings or with a derivative of this carboxylic acid which is activated on the carbonyl group.

3. A pharmaceutical containing a lipopeptide derivative according to formula I and pharmaceutical vehicles.

4. The use of a lipopeptide derivative according to formula I for producing a pharmaceutical for bacterial infections.

The invention is described in detail hereinafter, especially in its preferred embodiments. The invention is furthermore defined by the contents of the patent claims.

The starting compounds (compounds of the formula II) are obtained from the protected fermentation products, for

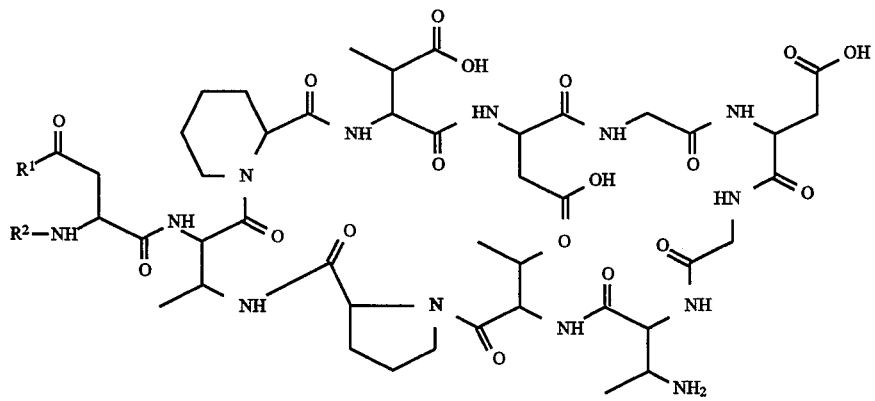

example from A 1437 β (I, $R^1$=OH, $R^2$=$(CH_3)_2CH(CH_2)_7CH$=$CHCH_2CO$) and 9-fluorenylmethyl chloroformate with the formation of the corresponding compound with

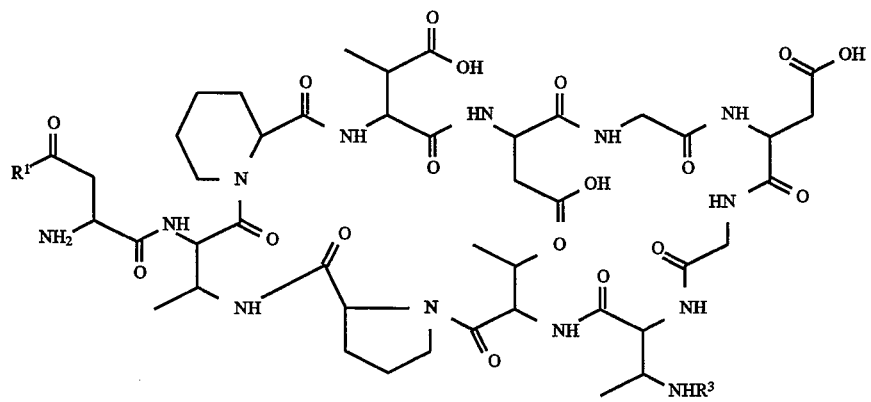

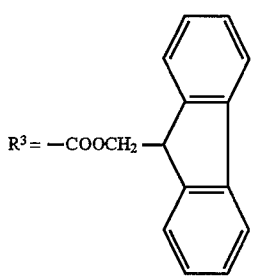

R³= —COOCH₂- and subsequent enzymatic elimination of the fatty acid residue by means of *Actinoplanes utahensis* NRRL 12052 (J. Antibiotics 1988, 1093).

If the carboxylic acids of the formula III are themselves employed as acylating agents it is expedient for a condensing agent, for example a carbodiimide such as N,N'-dicyclohexylcarbodiimide, to be present. The carboxylic acids of the formula II can be activated by the methods customary in peptide chemistry, as described, for example, in "Chemie in unserer Zeit" 27, 274–286 (1993). Accordingly, suitable activated derivatives are acid halides, for example acid chlorides, anhydrides or mixed anhydrides, for example with formic acid esters, azides, activated esters such as p-nitrophenyl, pentafluorophenyl, 4,6-dimethoxy-1,3,5-triazin-2-yl esters or esters with N-hydroxysuccinimide or 1-hydroxybenzotriazole which are obtained with carbodiimides as coupling reagents, or thioesters, for example with 2-mercaptobenzotriazole. Other suitable coupling reagents are N,N'-carbonyldiimidazole or those based on phosphonium or uronium salts such as, for example, BOP, HBTU, PyBOP, TBTU or TOTU (O-[cyano(ethoxycarbonyl)methylideneamino-1,1,3,3-tetramethyl] uronium tetrafluoroborate).

The reaction of the compounds of the formula II with a carboxylic acid of the formula III or activated derivatives thereof generally takes place in the presence of an inert solvent such as, for example, dichloromethane or dimethylformamide, preferably in the presence of a tertiary base such as, for example, pyridine or ethyldiisopropylamine. When substituted benzoyl chlorides are used it is also possible for water to be present and bases such as pyridine or sodium carbonate to be added. The reaction can take place in a temperature range from −20° to +50° C., preferably between −10° and +30° C.

The elimination of the protective groups R³ to form the compounds I takes place by processes known from the literature, for example the BOC group is eliminated with trifluoroacetic acid, the Z radical is eliminated with HBr/ glacial acetic acid or by catalytic hydrogenation, the Alloc group is eliminated with nucleophile plus Pd catalyst or the Fmoc group is eliminated with secondary amines, for example piperidine.

Preferred compounds of the formula I are those in which R² is a saturated aliphatic acyl radical $CH_3(CH_2)_nCO$, a branched saturated aliphatic acyl radical, preferably $(CH_3)_2CH(CH_2)_nCO$ or $CH_3CH_2CH(CH_3)(CH_2)_nCO$, an unsaturated aliphatic acyl radical which may contain one or more double bonds, it being possible for one double bond to be in the trans or cis form, preferably $H_2C=CH(CH_2)_nCO$, $(CH_3)_2CH(CH_2)_nCH=CH(CH_2)_nCO$, $CH_3(CH_2CH=CH)_n(CH_2)_nCO$, $CH_3(CH_2)_nCH=CH(CH_2)_nCH=CH(CH_2)_nCO$, $CH_3(CH_2)_nCH—CH—CO$, $CH_3(CH_2)_nCH=CH(CH_2)_nCO$ or $H(CH_2C(CH_3)=CHCH_2)_nCO$, an unsaturated aliphatic radical with one or more triple bonds, preferably $HC≡C(CH_2)_nCO$, $CH_3(CH_2)_nC≡C(CH_2)_nCO$, $CH_3(CH_2)_nC≡C—C≡C(CH_2)_nCO$, an aliphatic acyl radical which is interrupted by phenyl or cycloalkyl radicals, preferably

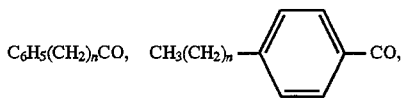

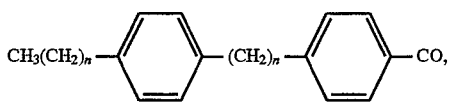

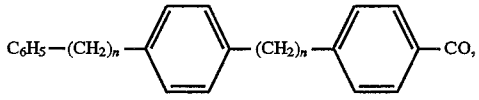

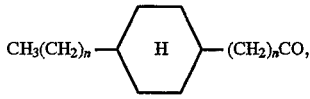

an acyl radical which is interrupted by an oxygen, preferably

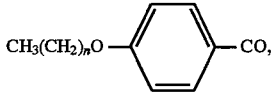

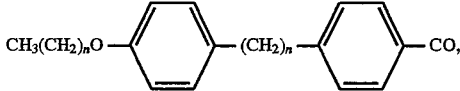

and in which n is integers between 0 and 20.

Particularly preferred compounds are those which have a straight-chain or branched $C_{12}$–$C_{15}$-acyl radical such as, for example, tetradecanoyl, tridecanoyl, 12-methyltridecanoyl, an unsaturated $C_{12}$–$C_{18}$-acyl radical with one or more double or triple bonds, such as, for example, cis-10-pentadecenoyl, trans-9-hexadecenoyl or $H(CH_2—C(CH_3)=CHCH_2)_3CO$ or an aliphatic acyl radical which is interrupted by 1–3 phenyl radicals and/or additionally by oxygen, such as, for example,

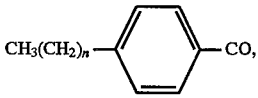

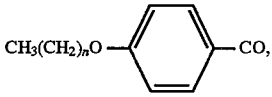

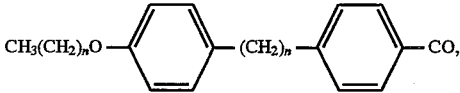

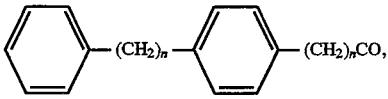

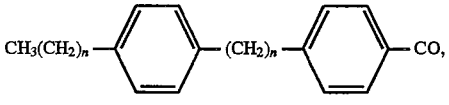

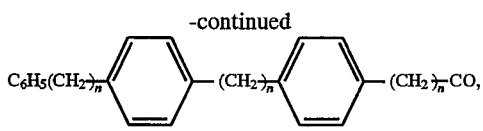

in which n are integers between 0 and 8.

Very particularly preferred compounds are those which contain an aliphatic acyl radical which is interrupted by 3 phenyl groups, such as, for example,

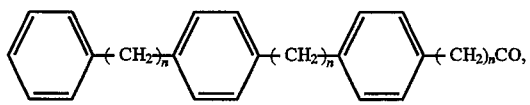

in which n are integers between 0 and 2.

The invention furthermore embraces a process for preparing compounds of the formula I which comprises reacting a compound of the formula II

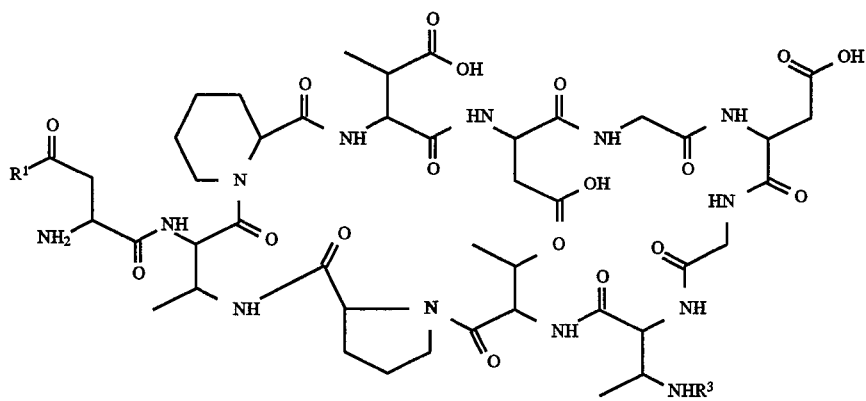

in which $R^1$ has the abovementioned meaning, and $R^3$ is an amino protective group known from peptide chemistry such as, for example, the tert-butoxycarbonyl (BOC), the benzyloxycarbonyl (Z, Cbz), the fluorenylmethoxycarbonyl (Fmoc) or the allyloxycarbonyl (Alloc) protective group, with a carboxylic acid of the formula III $R^2OH$             III in which $R^2$ has the abovementioned meanings.

Particularly useful pharmaceutically acceptable salts of the compounds of the formula I are salts with inorganic and organic acids, for example hydrochloric acid, sulfuric acid, acetic acid, citric acid, p-toluenesulfonic acid, with inorganic and organic bases such as NaOH, KOH, $Mg(OH)_2$, diethanolamine, ethylenediamine or with amino acids such as arginine, lysine, glutamic acid etc. They are prepared by standard methods.

One or more compounds of the lipopeptides according to the invention or their salts are suitable, by reason of their valuable pharmacological property, for use as pharmaceuticals.

The substances according to the invention have pharmacological activity, in particular as antibiotic for Gram-positive bacteria, particularly preferably for MRSA and glycopeptide-resistant strains.

A therapeutically adequate effect on penicillin- or methicillin-resistant strains (MRSA strains) which have developed further antibiotic resistances is often possessed only by glycopeptides such as vancomycin or teicoplanin. However, strains also resistant to these antibiotics are increasingly appearing (FEMS Microbiol. Lett. 98 (1992) 109 to 116). One or more compounds of the lipopeptides according to the invention have an excellent effect on these problem organisms too.

The invention also relates to pharmaceutical compositions of one or more compounds of the lipopeptides according to the invention or their salts.

One or more compounds of the lipopeptides according to the invention, preferably one or more compounds with three phenyl radicals in the acyl radical $R^2$ can in principle be administered undiluted as such. The preferred use is mixed with suitable ancillary substances, carrier material or diluents. It is possible to use as carrier material in veterinary pharmaceuticals the customary foodstuff mixtures or, in the case of humans, all pharmacologically acceptable carrier materials and/or ancillary substances.

The pharmaceuticals according to the invention are generally administered orally or parenterally, but rectal use is also possible in principle. Examples of suitable solid or liquid pharmaceutical formulations are granules, powders, tablets, coated tablets, (micro) capsules, suppositories, syrups, emulsions, suspensions, aerosols, drops or injectable solutions in ampoule form as well as products with protracted release of active substance, in the production of which there is normally use of excipients and additives and/or aids such as disintegrants or binders, coating and swelling agents, glidants or lubricants, flavorings, sweeteners or solubilizers. Examples of frequently used excipients or ancillary substances which may be mentioned are magnesium carbonate, titanium dioxide, lactose, mannitol and other sugars, talc, lactalbumin, gelatin, starch, vitamins, cellulose and its derivatives, animal or vegetable oils, polyethylene glycols and solvents such as, for example, sterile water, alcohols, glycerol and polyhydric alcohols.

Examples of diluents which may be mentioned are polyglycols, ethanol and water. Examples of buffer substances are organic compounds such as, for example, N,N'-dibenzylethylenediamine, diethanolamine, ethylenediamine, N-methylglucamine, N-benzylphenethylamine, diethylamine, tris(hydroxymethyl)aminomethane, or inorganic compounds such as, for example, phosphate buffer, sodium bicarbonate, sodium carbonate. It is also possible to administer the active substances as such in suitable form without excipient or diluent. Suitable doses of the compounds of the formula I or their pharmaceutically acceptable salts are about 0.4 g, preferably 0.5 g, to a maximum of 20 g per day for an adult of body weight approximately 75 kg. It is possible to administer single doses or, in general, multiple doses, and the single dose may contain the active substance in an amount of about 50 to 1000 mg.

The dosage units for oral administration may, where appropriate, be microencapsulated so that release is delayed or extended over a longer period, such as, for example, by coating or embedding the active substance in particulate form in suitable polymers, waxes or the like.

The pharmaceutical products are preferably produced and administered in dosage units, with each unit containing as active ingredient a particular dose of one or more compounds of the lipopeptides according to the invention. In solid dosage units such as tablets, capsules and suppositories, this dose can be up to about 200 mg, but preferably about 0.1 to 100 mg, and in injection solutions in ampoule form it is up to about 200 mg, but preferably up to 0.5 to 100 mg, per day.

The daily dose to be administered depends on the body weight, age, sex and condition of the mammal. However, higher or lower daily doses may also be appropriate in some circumstances. Administration of the daily dose may take place either by a single administration in the form of a single dosage unit or in a plurality of smaller dosage units, as well as by multiple administration of divided doses at particular intervals.

The pharmaceuticals according to the invention are produced by converting one or more compounds of the lipopeptides according to the invention with customary excipients and, where appropriate, additives and/or ancillary substances into the, or a, suitable administration form.

The particularly preferred compounds of the formula I with 3 phenyl radicals in the acyl radical $R^2$ (for example 55, 56) furthermore have particularly favorable toxicological properties. Thus, in the standard hemolysis test they show virtually no evidence of hemolysis while all tested compounds with straight-chain or branched aliphatic acyl radicals, including the natural substances, display a considerable activity between 16 and 25% (Table 1).

TABLE 1

| Hemolytic activity in vitro[2) | |
|---|---|
| Example | Hemolysis (%) |
| A 1437[1) | 17.5 |
| X CF$_3$CO$_2$H | |
| 1 | 19.6 |
| 6 | 16.5 |
| 7 | 25.7 |
| 8 | 19.3 |
| 9 | 22.8 |
| 14 | 22.9 |
| 49 | 0.0 |
| 55 | 0.5 |
| 56 | 0.4 |

[1)]Fermentation product I ($R^1$ = OH, $R^2$ = (CH$_3$)$_2$CH(CH$_2$)$_7$CH = CHCH$_2$CO)
[2)]Freshly removed venous blood from rhesus monkeys is used to measure the hemolytic activity. The blood is collected in heparinized tubes and 200 µl aliquots are distributed over 12 polyethylene tubes. 200 µl of distilled water are added to one aliquot, which serves as 100% standard, and another is mixed with 200 µl of physiological saline (0.9% NaCl) (0% standard.) 200 µl portions of substance dilutions in physiological saline containing 1600, 800, 400, 200, 100, 50, 25, 12.5, 6.25 and 3.125 mg/l are distributed over the other tubes. All the tubes are cautiously swirled and incubated at 37° C. for 3 hours. Subsequently 100% standard is made up with 5 ml of distilled water, and the others are each made up with 5 ml of physiological saline and centrifuged at 700 g for 5 minutes.

1) Fermentation product I ($R^1$=OH, $R^2$=(CH$_3$)$_2$CH(CH$_2$)$_7$CH=CHCH$_2$CO)

2) Freshly removed venous blood from rhesus monkeys is used to measure the hemolytic activity. The blood is collected in heparinized tubes and 200 µl aliquots are distributed over 12 polyethylene tubes. 200 µl of distilled water are added to one aliquot, which serves as 100% standard, and another is mixed with 200 µl of physiological saline (0.9% NaCl) (0% standard). 200 µl portions of substance dilutions in physiological saline containing 1600, 800, 400, 200, 100, 50, 25, 12.5, 6.25 and 3.125 mg/l are distributed over the other tubes. All the tubes are cautiously swirled and incubated at 37° C. for 3 hours. Subsequently 100% standard is made up with 5 ml of distilled water, and the others are each made up with 5 ml of physiological saline and centrifuged at 700 g for 5 minutes.

The hemolysis is determined by measuring the absorption of the supernatant in a spectrophotometer at a wavelength of 540 nm. The absorption of the standard with complete hemolysis (distilled water) is set equal to 100%. The absorptions of the test product dilutions and of the 0% standard are measured and reported as a percentage of the maximum inducible hemolysis.

The following examples of compounds which can be prepared according to the invention serve to illustrate the invention further.

The invention is illustrated further in the examples which follow. Percentage data are based on weight. Mixing ratios in the case of liquids are based on volume unless otherwise stated.

The purity of the reaction products is determined by analytical HPLC (Merck, Darmstadt, LiChrospher® 100RP-8, 125×4 mm, elution system water+trifluoroacetic acid pH 2.5, 0.1% sodium octanesulfonate/acetonitrile, detection with UV at 220 nm) and the structure was proven by electrospray mass spectroscopy (BIO-Q-MS).

For simplicity, the term A 1437 cyclic peptide is used below for the compound I with $R^2$=hydrogen.

EXAMPLE 1

Tridecanoyl Derivative of A 1437 Cyclic Peptide
(Compound I, $R^1$=HO, $R^2$=CH$_3$(CH$_2$)$_{11}$CO)

TOTU Coupling Process a) Activation of the tridecanoic acid: 113 mg (0.527 mmol) of tridecanoic acid are dissolved in 3.75 ml of N,N-dimethylformamide (DMF), and 172.5 mg (0.526 mmol) of TOTU and 1.25 g of a solution of ethyldiisopropylamine (0.5 mmol) in DMF (0.4 mmol/g) are added. The solution is left at room temperature for 1 hour.

b) Coupling: 348 mg (0.264 mmol) of Fmoc derivative II ($R^1$=OH, $R^3$=fluorenylmethoxycarbonyl; Example 69) are suspended in 7.2 ml of dry DMF, and 2.9 g of the activated solution a) (0.25 mmol) are added in an ice bath. The brownish solution which is formed is stirred at room temperature for 1.5 hours.

c) Elimination of the Fmoc protective group: Solution b) is cooled to 10°, 6 ml of piperidine are added, and the mixture is stirred at room temperature for 1 hour. It is then diluted with 250 ml of water and freeze dried.

d) Purification: The freeze-dried residue is suspended in 100 ml of water/acetonitrile (5:1), adjusted to pH 2.0 with 1.5 ml of 2N HCl, and the clear solution is chromatographed on 90 g of RP$_{18}$ silica gel (Merck, Art. 9303) with water+ 0.01% CF$_3$COOH/acetonitrile. Elution sequence: 500 ml of 3:1, 500 ml of 2:1 and 600 ml of 1:1 mixture. The title compound appears in the 1:1 fraction (UV detection 220 nm). Yield 267 mg (78% of theory) purity 72%.

The crude product is rechromatographed on a Büchi medium pressure column (250 g of RP$_{18}$, elution with water+0.01% CF₃COOH/acetonitrile (3:2)). The product fractions are freeze dried.

Yield: 130 mg, purity: 96% $C_{58}H_{93}N_{13}O_{20}$ [1292.5] MS: 1293

EXAMPLE 2

4-Octylbenzoyl Derivative of A 1437 Cyclic Peptide

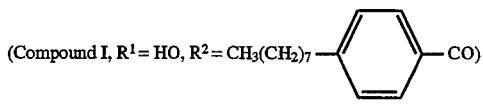

(Compound I, $R^1$ = HO, $R^2$ = CH₃(CH₂)₇—⟨⟩—CO)

Acid Chloride Process:

a) Coupling: 6.6 mg (0.005 mmol) of Fmoc derivative II (Example 69) are dissolved in 200 mg of pyridine/water (9:1) and, at −20° C., 25 mg (0.1 mmol) of 4-octylbenzoyl chloride are added. The solution is stirred at room temperature for 4 hours. After addition of 2 ml of dioxane, the solvent is removed in vacuo and the residue is dissolved in 0.2 ml of DMF.

b) Elimination of the Fmoc protective group: 0.2 ml of piperidine is added to solution a), and the mixture is left at room temperature for 1 hour. The solution is diluated with 5 ml of water and freeze dried.

c) Purification: The freeze-dried residue is chromatographed on 10 g of $RP_{18}$ silica gel with water+0.01% CF₃COOH/acetonitrile. Elution sequence: 80 ml of 3:1, 80 ml of 2:1 and 80 ml of 1:1 mixture. The 1:1 product fraction is freeze dried.

Yield: 4.6 mg (70% of theory), purity: 85% $C_{60}H_{89}N_{13}O_{20}$ [1312.5] MS: 1313

In analogy to Example 1, the compounds which are listed hereinafter and have the formula I in which $R^1$=HO and which carry the substituents $R^2$ indicated in Table 2 are obtained. The yields are between 60 and 85% of theory, and the purity is between 75 and 98%.

TABLE 2

| Example | $R^2$ | Molecular weight calculated | found |
|---|---|---|---|
| 3 | CH₃(CH₂)₆CO | 1222.3 | 1223 |
| 4 | CH₃(CH₂)₇CO | 1236.4 | 1237 |
| 5 | CH₃(CH₂)₈CO | 1250.4 | 1251 |
| 6 | CH₃(CH₂)₉CO | 1264.4 | 1265 |
| 7 | CH₃(CH₂)₁₀CO | 1278.4 | 1279 |
| 8 | CH₃(CH₂)₁₂CO | 1306.5 | 1307 |
| 9 | CH₃(CH₂)₁₃CO | 1320.5 | 1321 |
| 10 | CH₃(CH₂)₁₄CO | 1334.5 | 1335 |
| 11 | CH₃(CH₂)₁₅CO | 1348.6 | 1349 |
| 12 | CH₃CH(CH₃)(CH₂)₈CO | 1278.4 | 1279 |
| 13 | CH₃CH(CH₃)(CH₂)₉CO | 1295.5 | 1296 |
| 14 | CH₃CH(CH₃)(CH₂)₁₀CO | 1306.5 | 1307 |
| 15 | CH₃CH(CH₃)(CH₂)₁₂CO | 1334.5 | 1335 |
| 16 | H₂C═CH(CH₂)₈CO | 1262.4 | 1268 |
| 17 | H₂C═CH(CH₂)₉CO | 1276.4 | 1277 |
| 18 | CH₃(CH₂)₇CH═CHCO (trans) | 1262.4 | 1263 |
| 19 | CH₃(CH₂)₈CH═CHCO (trans) | 1276.4 | 1277 |
| 20 | CH₃(CH₂)₁₂CH═CHCO (trans) | 1332.5 | 1333 |
| 21 | CH₃(CH₂)₃CH═CH(CH₂)₇CO (cis) | 1304.5 | 1305 |
| 22 | CH₃(CH₂)₃CH═CH(CH₂)₇CO (trans) | 1304.5 | 1305 |
| 23 | CH₃(CH₂)₃CH═CH(CH₂)₈CO (cis) | 1318.5 | 1319 |
| 24 | CH₃(CH₂)₅CH═CH(CH₂)₇CO (cis) | 1332.5 | 1333 |
| 25 | CH₃(CH₂)₅CH═CH(CH₂)₇CO (trans) | 1332.5 | 1333 |
| 26 | CH₃(CH₂)₅CH═CH(CH₂)₈CO (cis) | 1346.6 | 1347 |
| 27 | CH₃(CH₂)₁₀CH═CH(CH₂)₄CO (cis) | 1360.6 | 1361 |
| 28 | CH₃(CH₂)₁₀CH═CH(CH₂)₄CO (trans) | 1360.6 | 1361 |
| 29 | CH₃(CH₂)₇CH═CH(CH₂)₇CO (cis) | 1360.6 | 1361 |
| 30 | CH₃(CH₂)₇CH═CH(CH₂)₇CO (trans) | 1360.6 | 1361 |
| 31 | CH₃(CH₂)₅CH═CH(CH₂)₉CO (trans) | 1360.6 | 1361 |
| 32 | CH₃(CH₂)₃(CH₂CH═CH)₂(CH₂)₇CO (cis) | 1358.6 | 1359 |
| 33 | CH₃(CH₂)₃(CH₂CH═CH)₂(CH₂)₂CO (trans) | 1358.6 | 1359 |
| 34 | CH₃(CH₂)₃(CH₂CH═CH)₂(CH₂)₉CO (cis) | 1386.6 | 1387 |
| 35 | CH₃(CH₂CH═CH)₃(CH₂)₇CO (cis) | 1356.5 | 1357 |
| 36 | CH₃(CH₂)₃(CH₂CH═CH)₃(CH₂)₄CO (cis) | 1356.5 | 1357 |

TABLE 2-continued

| Example | R² | Molecular weight calculated | found |
|---|---|---|---|
| 37 | CH₃(CH₂CH=CH)₄(CH₂)₄CO (cis) | 1354.5 | 1355 |
| 38 | CH₃(CH₂)₃(CH₂CH=CH)₄(CH₂)₃CO (cis) | 1382.6 | 1383 |
| 39 | CH₃(CH₂CH=CH)₆(CH₂)₂CO (cis) | 1406.8 | 1407 |
| 40 | HC≡C(CH₂)₈CO | 1260.4 | 1261 |
| 41 | CH₃(CH₂)₃C≡C(CH₂)₇CO | 1302.5 | 1303 |
| 42 | CH₃(CH₂)₇C≡C(CH₂)₇CO | 1358.6 | 1359 |
| 43 | CH₃(CH₂)₄—C≡C—C≡C—(CH₂)₈CO | 1354.6 | 1355 |
| 44 | ⌬—⌬—CH₂CO | 1290.4 | 1291 |
| 45 | ⌬—(CH₂)₉CO | 1326.5 | 1327 |
| 46 | ⌬—O—(CH₂)₁₀CO | 1356.5 | 1357 |
| 47 | (CH₃)₂C=CHCH₂[CH₂C(CH₃)=CHCH₂]₂CO | 1328.5 | 1329 |

In analogy to Example 2, the compounds which are listed hereinafter and have the formula I in which R¹=HO and which carry the substituents indicated in Table 3 are obtained. The yields are between 70 and 85% of theory and the purity is between 80 and 98%.

TABLE 3

| Example | R² | Molecular weight calculated | found |
|---|---|---|---|
| 48 | ⌬—⌬—CO | 1276.4 | 1277 |
| 49 | CH₃(CH₂)₆—⌬—CO | 1298.4 | 1299 |
| 50 | CH₃(CH₂)₆O—⌬—CO | 1314.4 | 1315 |
| 51 | CH₃(CH₂)₇—⌬—CO | 1312.5 | 1313 |
| 52 | CH₃(CH₂)₇O—⌬—CO | 1328.5 | 1329 |
| 53 | ⌬—(CH₂)₂—⌬—CO | 1304.4 | 1305 |

TABLE 3-continued

| Example | R² | Molecular weight calculated | found |
|---|---|---|---|
| 54 | CH₃CH₂—⟨C₆H₄⟩—(CH₂)₂—⟨C₆H₄⟩—CO | 1332.4 | 1333 |
| 55 | ⟨C₆H₅⟩—⟨C₆H₄⟩—(CH₂)₂—⟨C₆H₄⟩—CO | 1380.5 | 1381 |
| 56 | ⟨C₆H₅⟩—(CH₂)₂—⟨C₆H₄⟩—(CH₂)₂—⟨C₆H₄⟩—CO | 1408.6 | 1409 |
| 57 | CH₃(CH₂)₃—⟨C₆H₄⟩—(CH₂)₂—⟨C₆H₄⟩—CO | 1360.5 | 1361 |
| 58 | CH₃(CH₂)₅O—⟨C₆H₄⟩—(CH₂)₂—⟨C₆H₄⟩—CO | 1404.5 | 1405 |

In analogy to Example 1 (compounds 59–66) or Example 2 (compounds 67 and 68), the compounds which are listed hereinafter and have the formula I in which $R^1=NH_2$ and which carry the substituents $R^2$ indicated in Table 4 are obtained. The yields are between 75 and 85% of theory and the purity is between 80 and 98%.

TABLE 4

| Example | R² | Molecular weight calculated | found |
|---|---|---|---|
| 59 | CH₃(CH₂)₁₀CO | 1277.4 | 1278 |
| 60 | CH₃(CH₂)₁₁CO | 1291.5 | 1292 |
| 61 | CH₃(CH₂)₁₂CO | 1305.5 | 1306 |
| 62 | CH₃(CH₂)₁₃CO | 1319.5 | 1320 |
| 63 | CH₃CH(CH₃)(CH₂)₁₀CO | 1305.5 | 1306 |
| 64 | CH₃(CH₂)₃CH=CH(CH₂)₇CO (cis) | 1303.5 | 1304 |
| 65 | CH₃(CH₂)₃CH=CH(CH₂)₇CO (trans) | 1303.5 | 1304 |
| 66 | CH₃(CH₂)₂(CH₂CH=CH)₂(CH₂)₇CO (cis) | 1357.6 | 1358 |
| 67 | ⟨C₆H₅⟩—⟨C₆H₄⟩—(CH₂)₂—⟨C₆H₄⟩—CO | 1379.5 | 1380 |
| 68 | ⟨C₆H₅⟩—(CH₂)₂—⟨C₆H₄⟩—(CH₂)₂—⟨C₆H₄⟩—CO | 1407.6 | 1408 |

15
Preparation of the starting compounds

EXAMPLE 69

9-Fluorenylmethyloxycarbonyl Derivative of A 1437

($R^1$ = HO, $R^2$ = $(CH_3)_2CH(CH_2)_7CH=CHCH_2CO$,

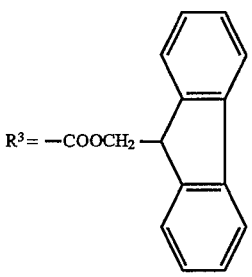

$R^3 = -COOCH_2-$ 10 g (7.67 mmol) of A 1437 (I, $R^1$=HO, $R^2$=$(CH_3)_2CH$ $(CH_2)_7CH$=$CHCH_2CO$) and 3.24 g (38.35 mmol) of sodium bicarbonate are dissolved in a mixture of 920 ml of water and 640 ml of acetone. Then, while monitoring the pH, a solution of 2.97 g (11.5 mmol) of 9-fluorenylmethyl chloroformate in 240 ml of acetone is added dropwise at pH 8.5 over the course of 100 minutes. During this the reaction solution warms to 27° C. It is then stirred at room temperature for 1 hour. After removal of the acetone in vacuo, the aqueous solution is freeze dried. The colorless residue is extracted by stirring twice with 500 ml of methylene dichloride each time to remove low molecular weight impurities.

Yield: 12.2 g, MS: 1526.7

EXAMPLE 70

9-Fluorenylmethyloxycarbonyl Derivative of A 1437 Cyclic Peptide (II, $R^1$=HO,

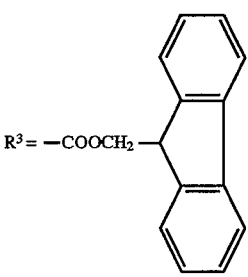

$R^3 = -COOCH_2-$

A mixture of 10 g of product from Example 69 and 300 g of wet *Actinoplanes utahensis* mycelium in 1 l of sterile potassium phosphate buffer (100 mmol, pH 7.2, 50 mmol EDTA, 0.02% sodium azide) is stirred at 32° C. for 48 hours. The biomass is then removed by centrifugation, the solution is filtered through 500 g of MCI gel (from Mitsubishi) to immobilize the product, and the product is eluted with water/methanol (1:1). The eluate is concentrated to remove methanol, and the aqueous phase is chromatographed on 500 g of $RP_{18}$ with water+0.05% trifluoroacetic acid/acetonitrile (2:1). The product fractions are concentrated in vacuo and freeze dried.

Yield: 6 g, MS: 1318.4

16

EXAMPLE 71

4-(2-(4-(2-Phenylethyl)phenyl)ethyl) benzoic Acid 33.9 g of triphenylphosphine are added to a solution of 22.9 g of methyl 4-bromomethylbenzoate in 1000 ml of toluene, and the mixture is heated under reflux. The reaction is complete after 7 hours. After cooling, the product is filtered off with suction.

Yield: 47.6 g

Stage 2

58.9 g of stage 1 are suspended in 500 ml of anhydrous tetrahydrofuran and cooled to 0° C., and 120 ml of a 1M solution of lithium bistrimethylsilylamide in tetrahydrofuran are added. After 1 hour at room temperature, the mixture is again cooled to 0° C., and 19.3 g of stilbene-4-aldehyde are added. The mixture is then stirred at 50° C. for 2.5 hours and cooled to 0° C., and the precipitated solid is filtered off with suction. The residue is washed with 0.5 l of THF. The organic phase is diluted with 750 ml of ethyl acetate and washed with 750 ml of saturated ammonium chloride solution. The aqueous phase is extracted with 750 ml of ethyl acetate, and the organic phase is dried over sodium sulfate and concentrated. The crude product is employed in the next stage.

Yield: 49.9 g

Stage 3

26.7 g of crude product from stage 2 are suspended together with 5 g of palladium on active carbon (10% Pd) in 1000 ml of methanol. Hydrogenation is carried out at room temperature under atmospheric pressure for 3 hours. The catalyst is filtered off hot, the solution is concentrated in vacuo, and the product is purified by chromatography on silica gel with heptane/ethyl acetate (10:1).

Yield: 7.4 g

Stage 4

1.98 g of stage 3 are suspended in 60 ml of ethanol, and a solution of 508 mg of KOH in 10 ml of water is added. The solution is heated under reflux for 1.5 hours. The ethanol is removed in vacuo, the residue is taken up in 500 ml of ethyl acetate and 200 ml of water, and the solution is adjusted to pH 2 with 2N HCl. The mixture is then stirred for 0.5 hours, the phases are separated, and the aqueous phases are extracted once more with 200 ml of ethyl acetate. The organic phases are combined, dried over sodium sulfate and concentrated in vacuo.

Yield: 1.86 g of the title compound

Acid Chloride:

1.23 g of stage 4 are suspended in 10 ml of thionyl chloride. The mixture is then heated under reflux until evolution of gas ceases. Cooling is followed by concentration in vacuo and evaporation twice with 5 ml of toluene each time.

Yield: 1.35 g of pale gray crystalline compound

EXAMPLE 72

4-(2-(4-Biphenylyl)ethyl)benzoic Acid

Stage 1:

In analogy to stage 2 in Example 71, 6.4 g of phosphonium bromide (stage 1 from Example 71) are reacted with 1.82 g of biphenyl-4-aldehyde.

Yield: 5.8 g

Stage 2:

5.8 g of stage 1 are hydrogenated in analogy to stage 3 in Example 71, and the product is purified by chromatography.

Yield: 970 mg

Stage 3:

950 mg of stage 2 are hydrolyzed in analogy to stage 4 in Example 71.

Yield: 880 mg

Stage 4:

850 mg of stage 3 are reacted with thionyl chloride in analogy to stage 5 in Example 71 to give the acid chloride.

Yield: 909 mg

We claim:

1. A lipopeptide A 1437 derivative of the formula I

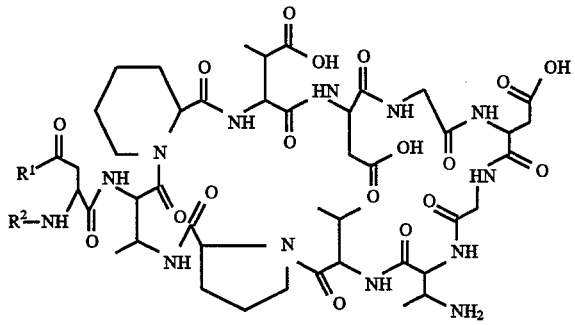

in which $R^1$ is OH or $NH_2$, $R^2$ is a straight-chain or branched, saturated or unsaturated aliphatic $C_8$–$C_{22}$-acyl radical which may be interrupted by phenyl or cycloalkyl groups or by oxygen, and pharmaceutically acceptable salts thereof.

2. A lipopeptide derivative as claimed in claim 1, wherein $R^2$ is a saturated aliphatic acyl radical $CH_3(CH_2)_nCO$, a branched saturated aliphatic acyl radical, an unsaturated aliphatic acyl radical which may contain one or more double bonds, it being possible for one double bond to be in the trans or cis form, $CH_3(CH_2)_nCH=CH(CH_2)_nCO$ or $H(CH_2C(CH_3)=CHCH_2)_nCO$, an unsaturated aliphatic radical with one or more triple bonds, an aliphatic acyl radical which is interrupted by phenyl or cycloalkyl radicals, an acyl radical which is interrupted by an oxygen, and in which n is integers between 0 and 20.

3. A lipopeptide derivative as claimed in claim 1, wherein $R^1$ is OH or $NH_2$, $R^2$ is a straight-chain or branched $C_{12}$–$C_{15}$-acyl radical, or an aliphatic acyl radical which is interrupted by 1–3 phenyl radicals and/or additionally by oxygen, and in which n is an integer between 0 and 8.

4. A lipopeptide derivative as claimed in claim 1, wherein $R^1$ is OH or $NH_2$, $R^2$ is an aliphatic acyl radical which is interrupted by 3 phenyl groups,

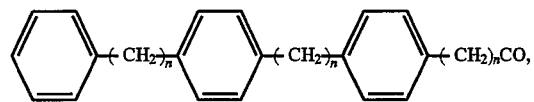

in which n is an integer between 0 and 2.

5. A process for preparing a compound of claim 1, which comprises reacting a compound of the formula II

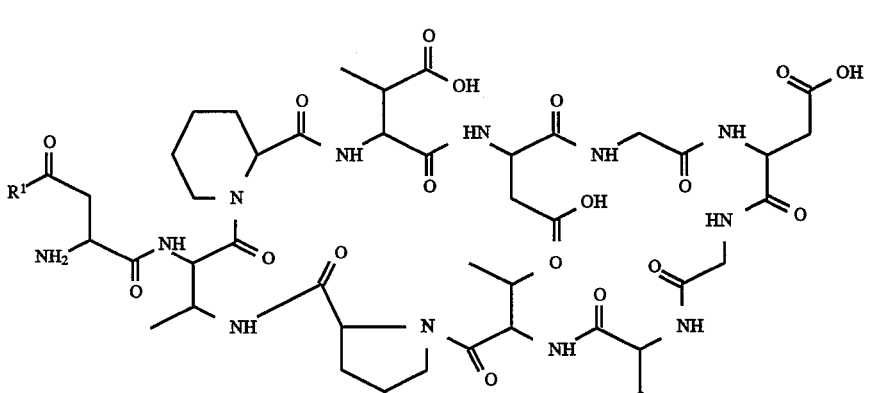

in which $R^1$ has the abovementioned meaning, and $R^3$ is an amino protective group known from peptide chemistry, that is the tert-butoxycarbonyl (BOC), the benzyloxycarbonyl (Z, Cbz), the fluorenylmethoxycarbonyl (Fmoc) or the allyloxycarbonyl (Alloc) protective group, with a carboxylic acid of the formula III $$R^2OH \quad\quad III$$

in which

R² has the meanings specified in claim 1
or with a derivative of this carboxylic acid which is activated on the carbonyl group.

6. A pharmaceutical comprising a lipopeptide derivative according to claim 1.

7. A pharmaceutical composition comprising a lipopeptide derivative according to claim 1 and a pharmaceutical vehicle.

8. A method for treating bacterial infections comprising administering an effective amount of a lipopeptide according to claim 1.

9. A lipopeptide derivative as claimed in claim 1, wherein when R² is a branched saturated aliphatic acyl radical, it is $(CH_3)_2CH(CH_2)_nCO$ or $CH_3CH_2CH(CH_3)(CH_2)_nCO$, and in which n is an integer between 0 and 20.

10. A lipopeptide derivative as claimed in claim 1, wherein when R² is an unsaturated aliphatic acyl radical which may contain one or more double bonds, it being possible for one double bond to be in the trans or cis form, it is $H_2C=CH(CH_2)_nCO$, $(CH_3)_2CH(CH_2)_nCH=CH(CH_2)_nCO$, $CH_3(CH_2CH=CH)_n(CH_2)_nCO$, $CH_3(CH_2)_nCH=CH(CH_2)_nCH=CH(CH_2)_nCO$, $CH_3(CH_2)_nCH-CH-CO$, $CH_3(CH_2)_nCH=CH(CH_2)_nCO$ or $H(CH_2C(CH_3)=CHCH_2)_nCO$, and in which n is an integer between 0 and 20.

11. A lipopeptide derivative as claimed in claim 1, wherein when R² is an unsaturated aliphatic radical with one or more triple bonds, it is $HC\equiv C(CH_2)_nCO$, $CH_3(CH_2)_nC\equiv C(CH_2)_nCO$, or $CH_3(CH_2)_nC\equiv C-C\equiv C(CH_2)_nCO$, and in which n is an integer between 0 and 20.

12. A lipopeptide derivative as claimed in claim 1, wherein when R² is an aliphatic acyl radical which is interrupted by phenyl or cycloalkyl radicals it is

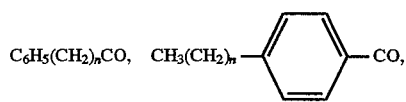

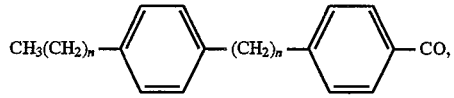

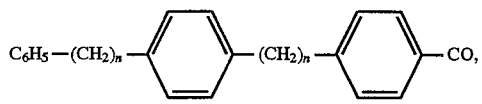

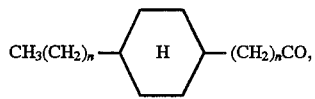

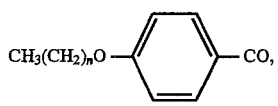

and in which n is an integer between 0 and 20.

13. A lipopeptide derivative as claimed in claim 1, wherein when R² is an acyl radical which is interrupted by an oxygen, it is

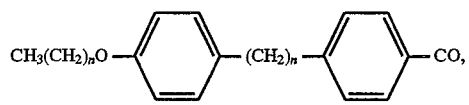

and in which n is an integer between 0 and 20.

14. A lipopeptide derivative as claimed in claim 1, wherein when R² is a straight-chain or branched $C_{12}-C_{15}$-acyl radical, it is tetradecanoyl, tridecanoyl or 12-methyltridecanoyl.

15. A lipopeptide derivative as claimed in claim 1, wherein when R² is an unsaturated $C_{12}C_{18}$-acyl radical with one or more double or triple bonds, it is cis-10-pentadecenoyl, trans-9-hexadecenoyl or $H(CH_2-C(CH_3)=CHCH_2)_3CO$.

16. A lipopeptide derivative as claimed in claim 1, wherein when R² is an aliphatic acyl radical which is interrupted by 1-3 phenyl radicals and/or additionally by oxygen, it is

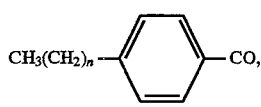

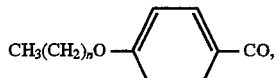

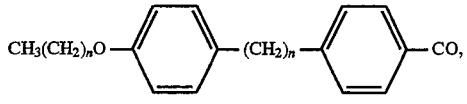

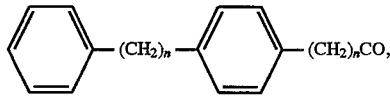

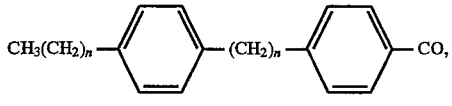

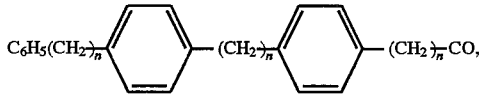

and in which n is an integer between 0 and 8.

17. The method according to claim 8, wherein said bacterial infection is a pencillin- or methicillin-resistant bacterial infection.

18. The method according to claim 8, wherein said bacterial infection is a glycopeptide-resistant bacterial infection.

19. The method according to claim 8, wherein said bacterial infection is a Gram-positive bacterial infection.

* * * * *